United States Patent
Mullins et al.

(10) Patent No.: US 9,365,858 B2
(45) Date of Patent: Jun. 14, 2016

(54) METHOD OF TRANSFORMING CELLS

(75) Inventors: Ewen Mullins, Carlow (IE); Toni Wendt, Carlow (IE); Fiona Doohan, Belfield (IE)

(73) Assignee: UNIVERSITY COLLEGE DUBLIN, NATIONAL UNIVERSITY OF IRELAND, Dublin (IE)

( * ) Notice: Subject to any disclaimer, the term of this patent is extended or adjusted under 35 U.S.C. 154(b) by 647 days.

(21) Appl. No.: 13/518,823

(22) PCT Filed: Dec. 23, 2010

(86) PCT No.: PCT/EP2010/070681
§ 371 (c)(1),
(2), (4) Date: Sep. 28, 2012

(87) PCT Pub. No.: WO2011/076933
PCT Pub. Date: Jun. 30, 2011

(65) Prior Publication Data
US 2013/0078706 A1    Mar. 28, 2013

Related U.S. Application Data

(60) Provisional application No. 61/289,853, filed on Dec. 23, 2009.

(30) Foreign Application Priority Data

Dec. 23, 2009    (EP) .................................... 09180700

(51) Int. Cl.
| | | |
|---|---|---|
| *C12N 15/82* | (2006.01) |
| *C12N 15/84* | (2006.01) |
| *C12R 1/01* | (2006.01) |
| *C12N 15/74* | (2006.01) |

(52) U.S. Cl.
CPC ............ *C12N 15/8202* (2013.01); *C12N 15/74* (2013.01); *C12R 1/01* (2013.01)

(58) Field of Classification Search
None
See application file for complete search history.

(56) References Cited

PUBLICATIONS

Broothaerts et al. (2005 Nature, 433 629-633).*
Kuhn et al. (Appl. Environ. Microbiol. 72 (2), 1248-1257 (2006)).*
Jefferson et al. GenBank: EF042581.1 (2006).*
Rudder et al. BMC Genomics 2014, 15:268 1-17.*

* cited by examiner

*Primary Examiner* — Anne Kubelik
*Assistant Examiner* — Charles Logsdon
(74) *Attorney, Agent, or Firm* — Cotman IP Law Group, PLC

(57) ABSTRACT

Use of an isolated *Ensifer adhaerens* strain OV14 deposited under NCIMB Accession Number 4177, or an isolated variant thereof characterized by a 16S rRNA gene having at least 98.6% sequence homology with SEQUENCE ID NO: 1, as a gene delivery system in the genetic transformation of a plant cell or plant material is described.

16 Claims, 11 Drawing Sheets

Figure 1

Bacteria
- Proteobacteria
  - Alphaproteobacteria
    - Brevundimonas
    - Rhizobiales
      - Phyllobacteriaceae
        - Aminobacter sp. Ml-p2a
        - Mesorhizobium loti
      - Rhizobiaceae
        - Sinorhizobium/Ensifer group
          - Ensifer adhaerens   *
          - Sinorhizobium meliloti
        - Rhizobium/Agrobacterium group
          - Rhizobium sp. NGR234 (rhizobium ngr234)
          - Agrobacterium tumefaciens
  - Gammaproteobacteria
    - Stenotrophomonas sp. Fa6
    - Enterobacteriaceae
      - Pantoea sp. 57917 (Pantoea sp. 57917)
      - Kluyvera intermedia
      - Enterobacter
        - Enterobacter sp. M9K1015
        - Enterobacter amnigenus (Enterobacter amnigenus)
    - Pseudomonas
      - Pseudomonas sp. LAB-26
      - Pseudomonas fulva
- Paenibacillus sp. B2a (Paenibacillus sp. B2a)

SEQUENCE LISTING

```
<160> NUMBER OF SEQ ID NOS: 7

<210> SEQ ID NO 1
<211> LENGTH: 684
<212> TYPE: DNA
<213> ORGANISM: Ensifer adherens OV14
<220> FEATURE:
<221> NAME/KEY: misc_feature
<222> LOCATION: (1)..(684)
<223> OTHER INFORMATION: 16s rRNA gene

<400> SEQUENCE: 1
gcctgatcag ccatgccgcg tgagtgatga aggccctagg gttgtaaagc tctttcaccg      60
gtgaagataa tgacggtaac cggagaagaa gccccggcta acttcgtgcc agcagccgcg     120
gtaatacgaa gggggctagc gttgttcgga attactgggc gtaaagcgca cgtaggcgga     180
catttaagtc aggggtgaaa tcccagagct caactctgga actgcctttg atactgggtg     240
tctagagtat ggaagaggtg agtggaattc cgagtgtaga ggtgaaattc gtagatattc     300
ggaggaacac cagtggcgaa ggcggctcac tggtccatta ctgacgctga ggtgcgaaag     360
cgtggggagc aaacaggatt agataccctg gtagtccacg ccgtaaacga tgaatgttag     420
ccgtcgggca gtttactgtt cggtggcgca gctaacgcat taaacattcc gcctggggag     480
tacggtcgca agattaaaac tcaaaggaat tgacggggc ccgcacaagc ggtggagcat     540
gtggtttaat tcgaagcaac gcgcagaacc ttaccagccc ttgacatccc gatcgcggat     600
tacagagatg tattccttca gttcggctgg atcggagaca ggtgctgcat ggctgtcgtc     660
agctcgtgtc gtgagatgtt gggt                                            684

<210> SEQ ID NO 2
<211> LENGTH: 686
<212> TYPE: DNA
<213> ORGANISM: Ensifer adhaerens E9954
<220> FEATURE:
<221> NAME/KEY: misc_feature
<222> LOCATION: (1)..(686)
<223> OTHER INFORMATION: 16S rRNA gene

<400> SEQUENCE: 2
gcctgccgcg tgagtgatga cggccctagg gttgtaaagc tctttcaccg gtgaagataa      60
tgacggtaac cggagaagaa gccccggcta acttcgtgcc agcagccgcg gtaatacgaa     120
gggggctagc gttgttcgga attactgggc gtaaagcgca cgtaggcgga catttaagtc     180
aggggtgaaa tcccggggct caacccccgga actgcctttg atactgggtg tctagagtat     240
```

-continued

```
ggaagaggtg agtggaattc cgagtgtaga ggtgaaattc gtagatattc ggaggaacac      300
cagtggcgaa ggcggctcac tggtccatta ctgacgctga ggtgcgaaag cgtggggagc      360
aaacaggatt agataccctg gtagtccacg ccgtaaacga tgaatgttag ccgtcgggca      420
gtttactgtt cggtggcgca gctaacgcat taaacattcc gcctgggag tacggtcgca       480 agattaaaac tcaaaggaat tgacgggggc cgcacaagc ggtggagcat gtggtttaat       540
tcgaagcaac gcgcagaacc ttaccagccc ttgacatccc gatcgcggat tacagagacg      600
ttttccttca gttcggctgg atcggagaca ggtgctgcat ggctgtcgtc agctcgtgtc      660
gtgagatgtt gggttaagtc ccgcaa                                           686
```

```
<210> SEQ ID NO 3
<211> LENGTH: 629
<212> TYPE: DNA
<213> ORGANISM: Ensifer adhaerens E20582
<220> FEATURE:
<221> NAME/KEY: misc_feature
<222> LOCATION: (1)..(629)
<223> OTHER INFORMATION: 16S rRNA gene
<220> FEATURE:
<221> NAME/KEY: misc_feature
<222> LOCATION: 506
<223> OTHER INFORMATION: n = a, c, g, or t

<400> SEQUENCE: 3
```

```
tgaagataat gacggtaacc ggagaagaag ccccggctaa cttcgtgcca gcagccgcgg       60
taatacgaag ggggctagcg ttgttcggaa ttactgggcg taaagcgcac gtaggcggac      120
atttaagtca ggggtgaaat cccgggggctc aaccccggaa ctgcctttga tactgggtgt    180
ctagagtatg gaagaggtga gtggaattcc gagtgtagag gtgaaattcg tagatattcg     240
gaggaacacc agtggcgaag gcggctcact ggtccattac tgacgctgag gtgcgaaagc     300
gtggggagca aacaggatta gataccctgg tagtccacgc cgtaaacgat gaatgttagc     360
cgtcgggcag tttactgttc ggtggcgcag ctaacgcatt aaacattccg cctggggagt    420
acggtcgcaa gattaaaact caaaggaatt gacgggggcc cgcacaagcg gtggagcatg    480
tggtttaatt cgaagcaacg cgcagnacct taccagccct tgacatcccg atcgcggatt    540
acggagacgt tttccttcag ttcggctgga tcggagacag gtgctgcatg gctgtcgtca     600
gctcgtgtcg tgagatgttg ggttaagtc                                       629
```

```
<210> SEQ ID NO 4
<211> LENGTH: 588
<212> TYPE: DNA
<213> ORGANISM: Ensifer adhaerens E20216
<220> FEATURE:
<221> NAME/KEY: misc_feature
<222> LOCATION: (1)..(588)
<223> OTHER INFORMATION: 16S rRNA gene

<400> SEQUENCE: 4
```

```
gagaagaagc cccggctaac tttcgtgcca gcagccgcgg taatacgaag ggggctagcg       60
ttgttcggaa ttactgggcg taaagcgcac gtaggcggac atttaagtca ggggtgaaat     120 cccgggggctc aaccccggaa ctgcctttga tactgggtgt ctagagtatg gaagaggtga    180
gtggaattcc gagtgtagag gtgaaattcg tagatattcg gaggaacacc agtggcgaag    240
gcggctcact ggtccattac tgacgctgag gtgcgaaagc gtggggagca aacaggatta    300
gataccctgg tagtccacgc cgtaaacgat gaatgttagc cgtcgggcag tttactgttc     360
```

| | |
|---|---|
| ggtggcgcag ctaacgcatt aaacattccg cctggggagt acggtcgcaa gattaaaact | 420 |
| caaaggaatt gacggggggcc cgcacaagcg gtggagcatg tggtttaatt cgaagcaacg | 480 |
| cgcaaaacct taccagccct tgacatcccg atcgcggatt acggagacgt tttccttcag | 540 |
| ttcggctgga tcggagacag gtgctgcatg gctgtcgtca gctcgtgt | 588 |

<210> SEQ ID NO 5
<211> LENGTH: 630
<212> TYPE: DNA
<213> ORGANISM: Ensifer adhaerens E10007
<220> FEATURE:
<221> NAME/KEY: misc_feature
<222> LOCATION: (1)..(630)
<223> OTHER INFORMATION: 16S rRNA gene

<400> SEQUENCE: 5

| | |
|---|---|
| cggtgaagat aatgacggta accggagaag aagccccggc taacttcgtg ccagcagccg | 60 |
| cggtaatacg aagggggcta gcgttgttcg gaattactgg gcgtaaagcg cacgtaggcg | 120 |
| gacatttaag tcagggtga aatcccgggg ctcaaccccg gaactgcctt tgatactggg | 180 |
| tgtctagagt atggaagagg tgagtggaat tccgagtgta gaggtgaaat tcgtagatat | 240 |
| tcggaggaac accagtggcg aaggcggctc actggtccat tactgacgct gaggtgcgaa | 300 |
| agcgtgggga gcaaacagga ttagatacccc tggtagtcca cgccgtaaac gatgaatgtt | 360 |
| agccgtcggg cagtttactg ttcggtggcg cagctaacgc attaaacatt ccgcctgggg | 420 |
| agtacggtcg caagattaaa actcaaagga attgacgggg gcccgcacaa gcggtggagc | 480 |
| atgtggttta attcgaagca acgcgcagaa ccttaccagc ccttgacatc ccgatcgcgg | 540 |
| attacagaga tgttttcctt cagttcggct ggatcggaga caggtgctgc atggctgtcg | 600 |
| tcagctcgtg tcgtgagatg ttgggttaag | 630 |

<210> SEQ ID NO 6
<211> LENGTH: 20
<212> TYPE: DNA
<213> ORGANISM: Artificial Sequence
<220> FEATURE:
<222> LOCATION: (1)..(20)
<223> OTHER INFORMATION: Synthetic
<220> FEATURE:
<221> NAME/KEY: prim_transcript
<222> LOCATION: (1)..(20)
<223> OTHER INFORMATION: E adhaerens 16S rRNA gene left primer

<400> SEQUENCE: 6

| | |
|---|---|
| tcggaattac tgggcgtaaa | 20 |

<210> SEQ ID NO 7
<211> LENGTH: 27
<212> TYPE: DNA
<213> ORGANISM: Artificial Sequence
<220> FEATURE:
<222> LOCATION: (1)..(27)
<223> OTHER INFORMATION: Synthetic
<220> FEATURE:
<221> NAME/KEY: prim_transcript
<222> LOCATION: (1)..(27)
<223> OTHER INFORMATION: E adherens 16S rRNA gene right primer

<400> SEQUENCE: 7

| | |
|---|---|
| cgaactgaag gaatacatct ctgtaat | 27 |

METHOD OF TRANSFORMING CELLS

INTRODUCTION

The invention relates to methods of producing transformed cells, especially transformed plant cells and plant tissue. The invention also relates to a strain of bacteria capable of producing transformed cells, and transformed plant cells and tissue.

BACKGROUND TO THE INVENTION

First introduced in 1997, over 125 million hectares of licensed genetically modified (GM) crops were grown across the globe in 2008 (www.isaaa.org). The primary method used to develop GM crops is dependent on using the soil inhabiting bacteria *Agrobacterium tumefaciens* to transfer a select gene(s) of interest (e.g. a gene conferring resistance to drought) into a specific plant (e.g. wheat).

Termed *Agrobacterium tumefaciens* mediated transformation (ATMT), the process of generating GM plants using *Agrobacterium tumefaciens* is comprehensively patented by the agri-biotech industry for the majority of the globe's commodity crops (Nottenburg C, Rodriguez C R (eds) (2007) *Agrobacterium*-mediated gene transfer: A lawyer's perspective. Springer, N.Y.). So, it is of considerable importance both academically and commercially to identify and develop other viable non-*Agrobacterium* bacteria that are capable of mediating cellular transformation. Brooetharts et al. (Nature. 2005 Feb. 10; 433(7026):629-33) described the potential of three non-*Agrobacterium* strains to genetically transform plant (rice, tobacco and the model plant species *Arabidopsis*) tissue. However, the transformation efficiency of these "Transbacter" strains was poor relative to standard *Agrobacterium*-mediated transformation. For example; the best performing Transbacter strain (*Sinorhizobium meliloti*) transformed *Arabidopsis* at a rate representing 5-10% of *Agrobacterium*-mediated transformation and while Brooetharts et al. report transformation frequency in tobacco for the same strain at 28%-36%, this data only represents the recovery of un-rooted shoots. The issue of using bacteria strains such as Transbacter (and related *Rhizobia* spp.) is further compounded by the necessity for strain-specific optimisations as reported in Brooetharts et al. and Wendt et al. (Transgenic Research, DOI: 10.1007/s11248-010-9423-4 Online First™), which complicates transformation protocols relative to the conventional *Agrobacterium*-mediated transformation protocols that are widely practised. The low transformation efficiencies of rhizobia species are further demonstrated in Wendt et al., where the frequency (calculated as % of shoots equipped with root systems with the ability to grow in rooting media supplemented with 25 µg/ml hygromycin) of transforming potato with the *rhizobia* strains was calculated at 4.72, 5.85 and 1.86% for *S. meliloti*, R. sp. NGR234 and *M. loti* respectively. This differs significantly with an average transformation frequency of 47.6% for the *A. tumefaciens* control treatment.

International Patent Application No: PCT/US2007/069053 describes the use of a number of non-*Agrobacterium* strains to genetically transform plant tissue, including transformation of soy using *Sinorhizobium freddi* SF4404 which achieved a transformation efficiency of 0.04% and transformation of corn using *Sinorhizobium freddi* SF4404 and *Sinorhizobium freddi* SF542C which achieved a transformation efficiency of 5.17% and 1.61%, respectively. These contrast with available literature which indicates that ATMT of soybean and corn can achieve transformation efficiencies of up to 18% for soybean (Dang et al., Plant Science, 2007, 173; 381-389) and 22% for corn (Reyes et al., Plant Physiology, 2010, 153:624-631). This indicates that the *Sinorhizobium* mediated transformation of corn and soy would have a relative transformation efficiency (relative to ATMT) of about 7% to 30%. Similarly, for canola, Patent Application No: PCT/US2007/069053 reports a transformation efficiency of up to 1.33% (RL2370G), which is 18-fold less efficient than reported transformation efficiencies (up to 25%) for ATMT (Cardoza and Stewart, Plant Cell Reports, 2003, 21; 599-604). Thus, the literature clearly indicates that transformation efficiencies achieved using non-*Agrobacterium* mediated transformation are poor relative to *Agrobacterium*-mediated transformation, across a number of plants species.

It is an object of the present invention to overcome at least one of the above problems.

STATEMENTS OF INVENTION

Broadly, the invention relates to a method of plant transformation which employs a strain of *Ensifer adhaerens* as a gene delivery system. One example of the strain of *Ensifer adhaerens* is *Ensifer adhaerens* strain OV14 which was deposited at the NCIMB on 18 Nov. 2010 under reference NCIMB 41777. As described below, *Ensifer adhaerens* strain OV14, and variants thereof, have successfully transformed plant tissue with transformation efficiencies relative to *Agrobacterium* AGL1 mediated transformation of up to 100%.

The invention therefore relates to a use of *Ensifer adhaerens* strain OV14, or a variant thereof, as a gene delivery system in the genetic transformation of a plant cell or plant material.

The invention also relates to a method of producing a transgenic cell which comprises the steps of inoculating a cell with a strain of *Ensifer adhaerens* OV14, or a variant thereof, containing a transformation platform including a transgene, culturing the cell under conditions that enable the strain of *Ensifer adhaerens* to transform the cell, selectively screening the inoculated cells for transformed cells, and typically isolating the or each transformed cell. Typically, the transformation platform comprises a transformation vector that is equipped with a transgene.

The invention also relates to *Ensifer adhaerens* strain OV14 deposited at the NCIMB on 18 Nov. 2010 under reference NCIMB 41777, and isolated variants of the strain characterised by a 16S rRNA gene having greater than 99.2% sequence homology with SEQUENCE ID NO: 1 and which ideally have the ability to genetically transform an *Arabidopsis* plant with a transformation efficiency relative to *A. Tumefaciens* strain AGL1 of at least 10%, 15%, 18%, 20%, 30%, 40%, 50%, 60%, 70%, 80%, 90% or 100%.

The invention also relates to an isolated *Ensifer adhaerens* strain containing a transformation platform including a transgene.

The invention also relates to *Ensifer adhaerens* strain OV14 deposited at the NCIMB on 18 Nov. 2010 under reference NCIMB 41777, and isolated variants of the strain characterised by a 16S rRNA gene having greater than 98% sequence homology with SEQUENCE ID NO: 1, wherein the strain OV14 and the isolated variants contain a transformation platform including a transgene.

In another embodiment, the invention relates to a transgenic cell or plant cell, transgenic plant tissue, transgenic plant material, or stable transgenic plant, obtainable by the process of the invention.

In another embodiment, the invention relates to a kit of parts capable of genetically transforming a cell, ideally a plant cell, comprising (a) *Ensifer adhaerens* strain OV14, or a variant thereof, or a strain of *Ensifer adhaerens* of the invention, (b) a unitary transformation vector, and (c) a transgene. The transgene may be located on the unitary transformation vector or may be on a different vector. In a preferred embodiment, the transformation vector is selected from the group consisting of; pC5105 or a functional variant thereof.

Typically, the methods and uses of the invention produce stable transgenic plant tissue and/or stable transgenic plants, preferably stable transgenic plants selected from the group consisting of: *Arabidopsis*; potato (i.e. *Solanum tuberosum*); tobacco (*Nicotiana tabaccum*); *Glycine max; Brassica napus*; wheat; barley; maize and rice. As used herein, the term "stable transgenic plant" means that the plant includes a transgene which is stably incorporated into the host cells genome and stably expressed over at least two, three or four generations.

As used herein, the term "variant thereof" means a strain of *Ensifer adhaerens* (either a naturally occurring strain, or a naturally occurring strain that is genetically modified) characterised by a 16S rRNA gene having at least 98%, 98.6%, 99%, 99.1%, 99.2%, 99.3%, 99.4%, 99.5%, 99.6%, 99.7%, 99.8% or 99.9% sequence homology with SEQUENCE ID NO: 1 (which is the sequence of the 16S rRNA gene of *Ensifer adhaerens* strain OV14), and which is ideally capable of genetically transforming an *Arabidopsis* plant with a transformation efficiency relative to an *A. tumefaciens* strain AGL1 of at least 10%, 15%, 18%, 20%, 30%, 40%, 50%, 60%, 70%, 80%, 90%, 95%, 99% or 100%. The term "variants" typically also means *E. adhaerens* strains that retain the phenotypic characteristics of *E. adhaerens* OV14. The term should be understood to include genetically modified versions of the deposited strain in which the genetic code is manipulated by means of, for example, genetic engineering or other natural and non-natural means.

An *Ensifer adhaerens* strain having a 16S rRNA gene having at least 99.2% sequence homology with SEQUENCE ID NO: 1 is strain LMG9954. *Ensifer adhaerens* strains having a 16S rRNA gene having at least 98.6% sequence homology with SEQUENCE ID NO: 1 are strains LMG10007, LMG20582 and LMG20216.

Transformation efficiency is determined using the methods described herein. In particular, transformation efficiency is calculated based on the percentage of explants that generate callus in the presence of the antibiotic or explants that generated shoots in the presence of the antibiotic (See Table 2).

In this specification, the term "sequence homology" should be considered to include both sequence identity and similarity, i.e. a 16S rRNA gene sequence that shares at least 98% sequence homology with a reference sequence is one in which any 98% of aligned nucleotides at least are either identical to, or conservative substitutions of, the corresponding residues in the reference sequence.

Suitably, the cell to be transformed is obtained from a plant or fungus. Typically, the cell is obtained from a monocotyledon or dicotyledon plant. Preferably, the cell is obtained from a dicotyledon plant. In a particularly preferred embodiment, the cell is a plant cell selected from the group consisting of: *Arabidopsis*; potato (i.e. *Solanum tuberosum*); tobacco (*Nicotiana tabaccum*); *Glycine max; Brassica napus*; wheat; barley; maize and rice. In another embodiment of the invention, the cell is a fungal cell. Preferably, the fungal cell is selected from *Ascomycetes*, for example *Fusarium* spp, *Septoria tritici*. In one embodiment, the cell is a plant cell with the proviso that soy and corn plant cells are excluded. Ideally, the plant cell is selected from potato, tobacco and wheat. The methods and uses of the invention when applied to potato provide at least 40%, 50%, 60%, 70%, 80%, or 90% transformation efficiency relative *Agrobacterium* mediated transformation. The methods and uses of the invention when applied to tobacco provide at least 40%, 50%, 60%, 70%, 80%, or 90% transformation efficiency relative to ATMT. The methods and uses of the invention when applied to wheat provide at least 40%, 50%, 60%, 70%, 80%, or 90% transformation efficiency relative to ATMT. The methods and uses of the invention when applied to barley provide at least 40%, 50%, 60%, 70%, 80%, or 90% transformation efficiency relative to ATMT. The methods and uses of the invention when applied to maize provide at least 40%, 50%, 60%, 70%, 80%, or 90% transformation efficiency relative to ATMT. The methods and uses of the invention when applied to rice provide at least 40%, 50%, 60%, 70%, 80%, or 90% transformation efficiency relative to ATMT.

In this specification, the term "transformation platform" should be understood to mean the genetic machinery required to transfer a gene into cell. The transformation vector may be endogenous *Ensifer adhaerens* genes, or preferably is provided in the form of an exogenous transformation vector or vectors. Typically, the transformation vector comprises a Ti plasmid (or a fragment thereof), suitably containing a region of T-DNA and ideally at least one or more virulence genes. Preferably, the Ti plasmid or fragment thereof is obtained from *Agrobacterium*. Suitably, the transgene is incorporated into the T-DNA region of the Ti plasmid. More preferably, the transgene is incorporated between the left and right borders of the T-DNA region. The Ti plasmid may comprise a selectable marker gene, although this is not required as successful transformation with the transgene may be rapidly detected for example by means of high-throughput PCR. When employed, the selectable marker gene is suitably contained within the T-DNA region and ideally operatively linked to the transgene.

In this specification, the term "transgene" should be understood to mean genetic material that is capable of being incorporated into and modifying the genetic material of the host cell and is capable of being expressed by the transformed cell. In one embodiment of the invention, the transgene may confer resistance to the host cell to, for example, a specific biotic stress (e.g. fungal, viral, bacteria, insect infection) and/or abiotic stress (e.g. drought resistance, blight resistance). In one embodiment, the transgene confers antibiotic resistance, the antibiotic resistance suitably being selected from resistance to antibiotics such as hygromycin, kanamycin, spectinomycin, tetracycline or ampicillin.

In another embodiment of the invention, the transgene may facilitate the transfer of non-agronomic traits. Suitably, the transgene encodes non-agronomic proteins including antibodies for vaccines, micronutrients (e.g. folic acid, vitamin A), bio-pharmaceutical or veterinarian drugs. Preferably, the transgene is selected from a group comprising; RB (Song, J. et al. Proc Natl Acad Sci (2003) 100(16) 9128-9133), hph, Neomycin phosphotransferase II [NPT II/Neo]), aadA and tetR. Other suitable transgenes will be known to those skilled in the art.

Preferably, the transformation platform or vector comprises a Ti plasmid containing a region of T-DNA, wherein the transgene is located within the T-DNA region, ideally between the left and right borders of the T-DNA region. In one embodiment, the transgene is operatively linked to a selectable marker gene. The term "operatively linked" should be understood to mean that in transformed cells the selectable marker gene will be transferred with the transgene. In this specification, the term "selectable marker gene" is taken to mean an exogenous piece of genetic material that when incorporated into the host DNA will confer a detectable signal of effective transformation. In a preferred embodiment, the selectable marker gene is selected from a group comprising: hph, Neomycin phosphotransferase II [NPT II/Neo]), aadA and tetR. Appropriate reporter transgenes could include GUS or GFP.

In another embodiment, the transgene gene also functions as selectable marker gene, wherein the traits displayed by the transformed cell function as a selective marker for the successful incorporation of the transgene. For example the transgene may confer resistance to particular disease or antibiotic, wherein the transformed cell is identifiable by virtue of the fact that it is able to grow in conditions that would have previously not been viable. Typically, the antibiotic resistance is selected from resistance to antibiotics such as hygromycin, kanamycin, spectinomycin, tetracycline and ampicillin. Suitably the transgene confers resistance to disease including potato blight.

In a preferred embodiment, the transgene is not linked to selectable marker gene and detection of the successful incorporation of the transgene in the transformed plant is by means of PCR/high throughput genetic sequencing.

Preferably, the Ti plasmid contains one or more virulence genes, wherein the at least one virulence gene is typically selected from the group consisting of virA, virB, virC, virD, virE, virG, virK and virJ or functional variants thereof. Ideally, at least 6, 7 or 8 of the above virulence genes are contained on the transformation vector. Preferably, at least 6, 7 or 8 of the above virulence genes form part of the Ti plasmid. A functional variant of a virulence gene is a virulence gene that has been genetically modified by, for example, modification of one or more nucleotides, for example, in a process known in the art as "directed evolution".

In a preferred embodiment of the invention, the transformation platform is a unitary transformation vector. In this specification, the term "unitary (transformation) vector" generally means a single transformation vector comprising a Ti plasmid and a transgene and ideally the required number of virulence genes. Preferably the unitary transformation vector is pC5105 or a functional variant thereof (e.g. pC5106). The term "functional variant" should be understood to mean a derivative of pC5105 which retains the ability to successfully transform a cell when used in combination with *Agrobacterium tumefaciens* or *Ensifer adhaerens* strain OV14—an example of such a functional variant is pC5106. Most preferably, the transformation vector is pC5105. In another embodiment of the invention, the transformation vector is a binary vector system. In this specification, the term "binary vector system" is taken to mean a Ti plasmid containing the transgene and a neighbouring virulence plasmid containing the necessary vir genes to accommodate successful transformation. Binary vector system is an art recognised term and examples of binary vector systems will be known to those skilled in the art.

BRIEF DESCRIPTION OF THE FIGURES

FIG. 1: Phylogenetic analysis of candidate strains, including *Ensifer adhaerens* following 16s rRNA sequencing.

DETAILED DESCRIPTION OF THE INVENTION

Generally, the invention relates to the use of a class of bacteria, *E. adhaerens*, for the genetic transformation of cells, especially plant cells and fungal cells, more preferably plant tissue and plants. Use of the class of bacteria provides for the generation of stable transformation, and also surprisingly provides for up to 100% transformation efficiency relative to *Agrobacterium* mediated transformation. The class of bacteria is typically characterised by have a high degree of similarity to *E. Adhaerens* OV14, deposited at the NCIMB under Accession Number 41777, for example having a 16S rRNA gene which has at least 98.6% or 99.2% sequence homology (or ideally sequence identity) to SEQUENCE ID NO: 1. Use of the class of bacteria provides for (tobacco and potato) transformation efficiencies relative to *Agrobacterium* AGL1 of from 40% to 100%, which is highly surprising given the literature in the field. The use and methods of the invention are ideally suited for the genetic transformation of plant cells, and for the production of transformed plants, ideally stably transformed plants, typically selected from *Arabidopsis*; potato (i.e. *Solanum tuberosum*); tobacco (*Nicotiana tabaccum*); *Glycine max; Brassica napus*; wheat; barley; maize and rice.

*Ensifer adhaerens* strain OV14 was isolated from soil samples taken from around the root system (rhizosphere) of oilseed rape plants grown in Oak Park, Co. Carlow, Ireland, in the spring of 2008. The strain was deposited at the NCIMB in compliance with the Budapest Treaty on 18 Nov. 2010, under NCIMB Accession Number 41777. The name and address of the depository are NCIMB Ltd, Ferguson Building, Craibstone Estate, Bucksburn, Aberdeen AB21 9YA. The strain is characterised by a 16S rRNA gene sequence shown in SEQUENCE ID NO: 1.

Utilising the widely adopted 'floral dip' based transformation protocol, the potential of *Ensifer adhaerens* OV14 to transform the model species *Arabidopsis*, along with the universally used *Agrobacterium tumefaciens* strain (AGL1) and three other non-*Agrobacterium* strains (Transbacter™, *Sinorhizobium meliloti, Rhizobium* sp. NGR234 and *Mesorhizobium loti*) were tested.

Figure 2:
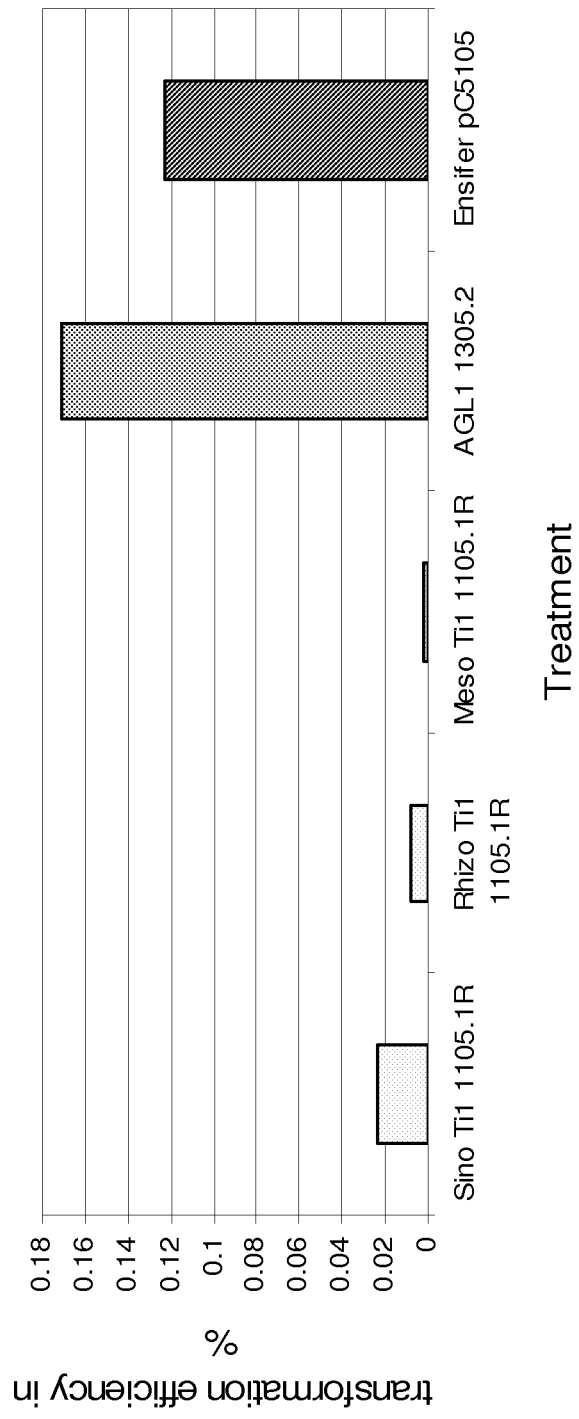
FIG. 2: Comparison of the transformation efficiencies of industry-used AGL1 against novel *Ensifer adhaerens* and other non-*Agrobacterium* species. Efficiency was calculated on the recovery of viable hygromycin resistant *Arabidopsis* seedlings from 150,000 $T_0$ seed screened.

In the first experiment the transformation efficiency of *Ensifer adhaerens* (~0.12) was 6-fold greater than the best reported *Rhizobia* strain (*Sinorhizobium meliloti*) (Brooetharts et al. 2005) (FIG. 2) and was equivalent to that of the *A. tumefaciens* AGL1 strain (~0.15). This result demonstrates that *Ensifer adhaerens* OV14 can genetically transform plant material at a rate similar to the *Agrobacterium*-based transformation system that is used globally by the research community.

Figure 3:
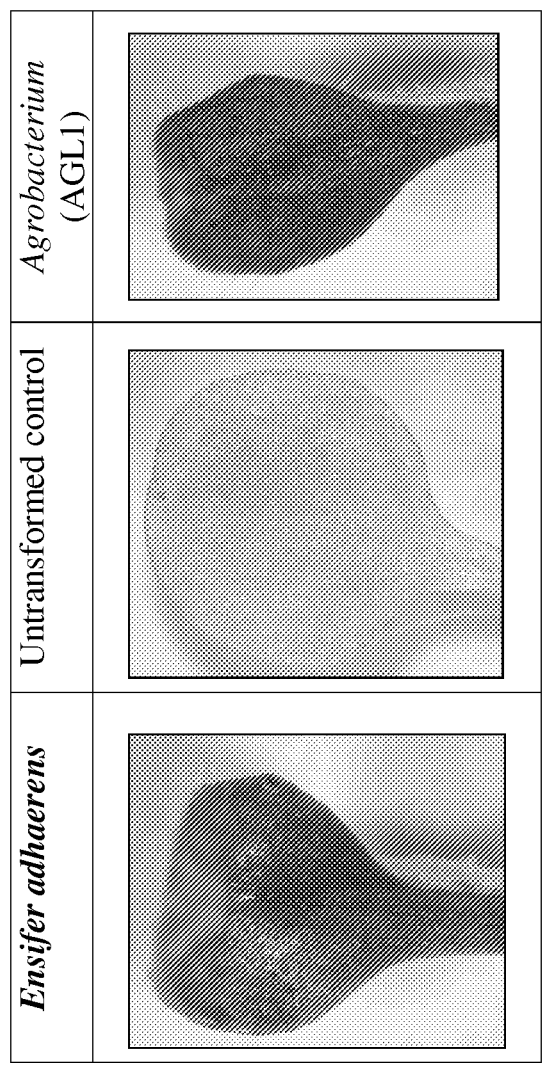
FIG. 3: Visual assessment of transformed tissues (stained blue with GUS reporter gene) following treatment with *Ensifer adhaerens*. Controls include untransformed leaf and *Agrobacterium*-treated.

Employing a specific reporter gene (GUS) in the transformation process, enabled a visual assessment of the transformed *Arabidopsis* tissues to be completed, with the presence of intense blue-coloured staining indicating plant tissues that have been successfully transformed (FIG. 3).

Figure 4:
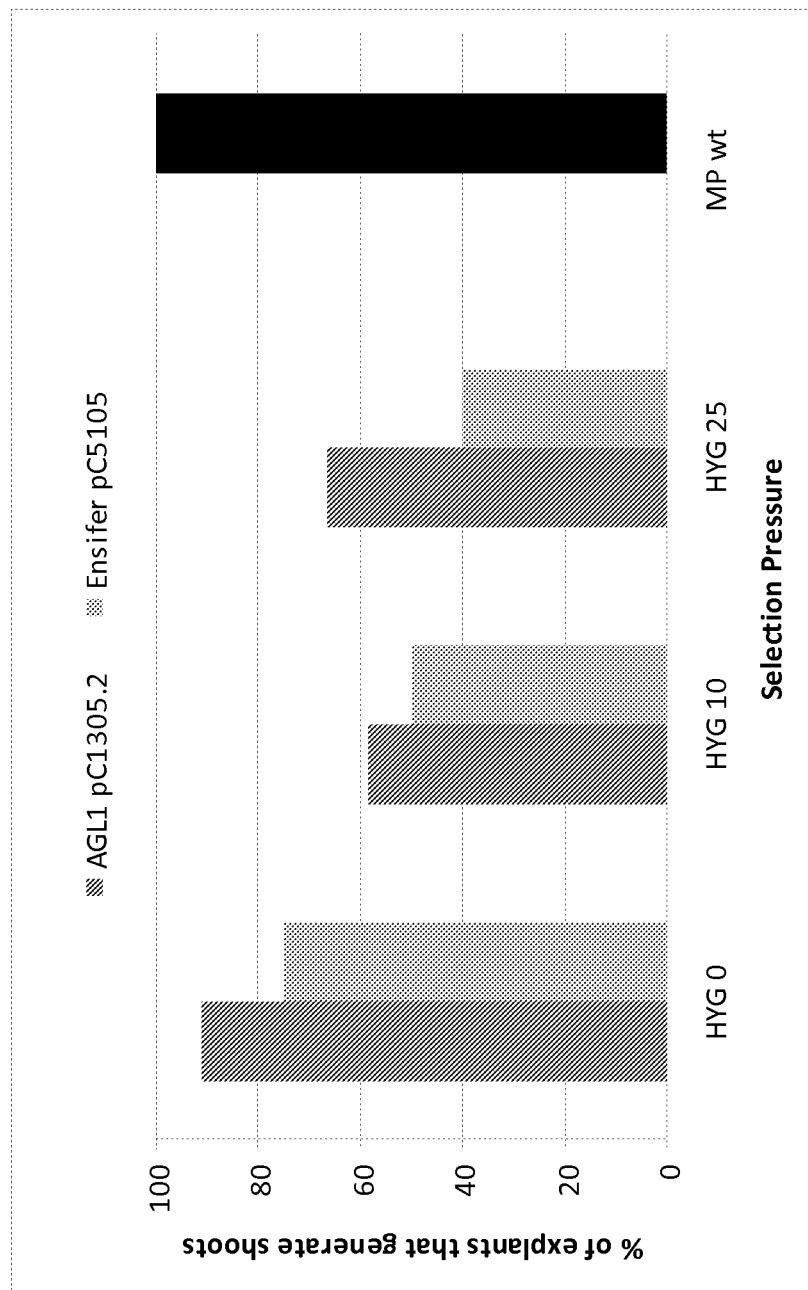
FIG. 4: Comparison of the transformation efficiency during shoot induction stage between *Agrobacterium tumefaciens* mediated transformation and *Ensifer* mediated transformation in potato in the presence of no antibiotic selection (HYG 0), low (HYG 10) and medium selection pressure (HYG 25).

*Solanum tuberosum* variety Maris Peer was successfully transformed using *Ensifer* pC5105 and antibiotic resistant potato lines were recovered. Transformation efficiencies during shoot induction stage (individual explants that generate shoots) show that *Ensifer*-mediated transformation (EMT) is 8.3% less efficient than *A. tumefaciens* when selected at 10 μg/ml hygromycinB (FIG. 4).

Figure 5:
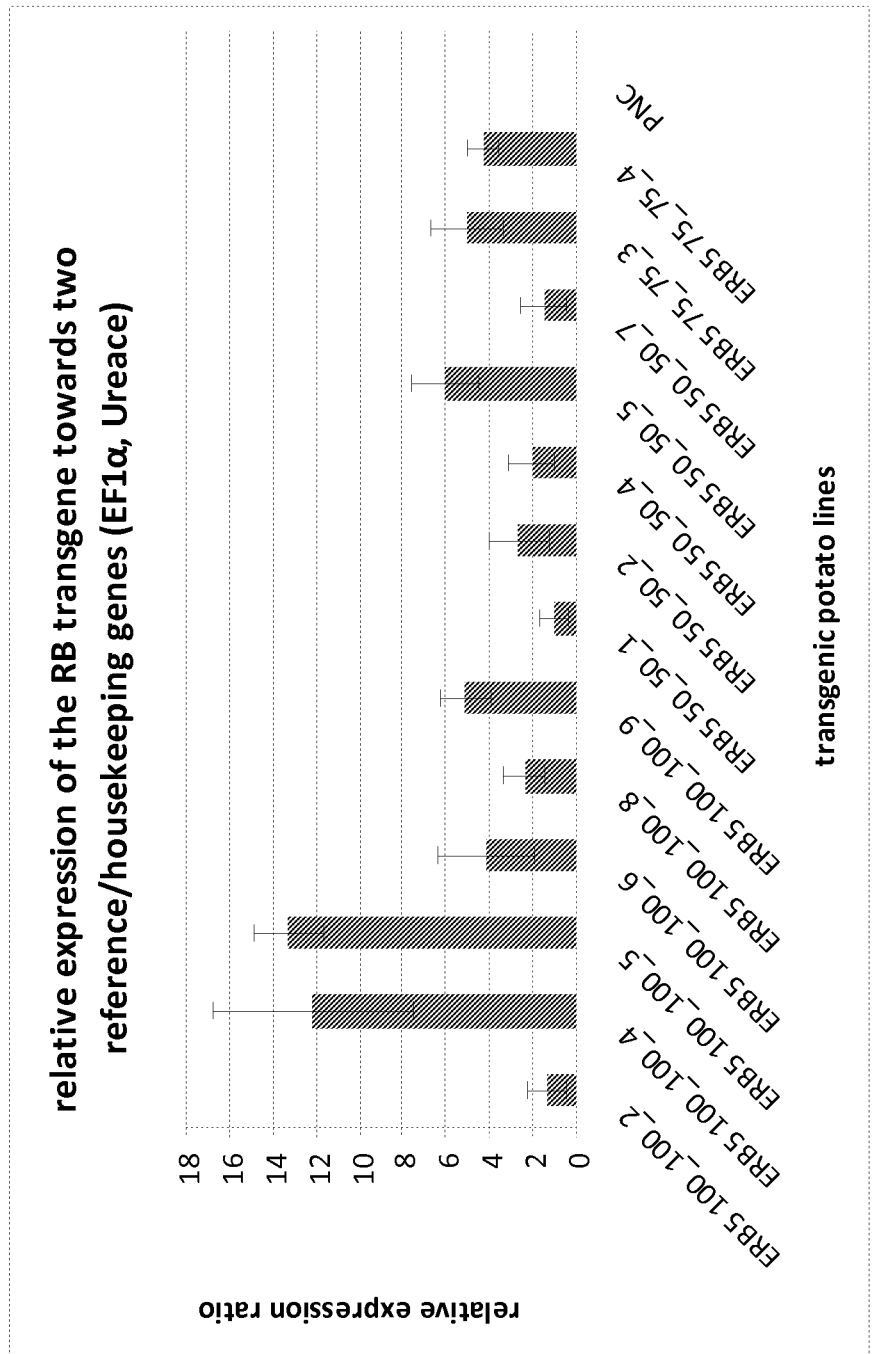
FIG. 5: Gene expression analysis of the RB transgene in different transgenic *Solanum tuberosum* var. Maris Peer lines generated via *Ensifer*-mediated transformation.

An *Ensifer* strain that carried a gene (RB) conferring resistance to late blight in potato via the pCLD04541 plasmid was also generated. This was used to transform the blight susceptible potato variety Maris Peer with *Ensifer adhaerens* containing the pC5105 plasmid and the pCLD04541 plasmid. The resulting blight resistant potato population was analysed using quantitative RT-PCR, thus showing the levels of gene expression in the different transgenic potato lines (FIG. 5).

Figure 6:
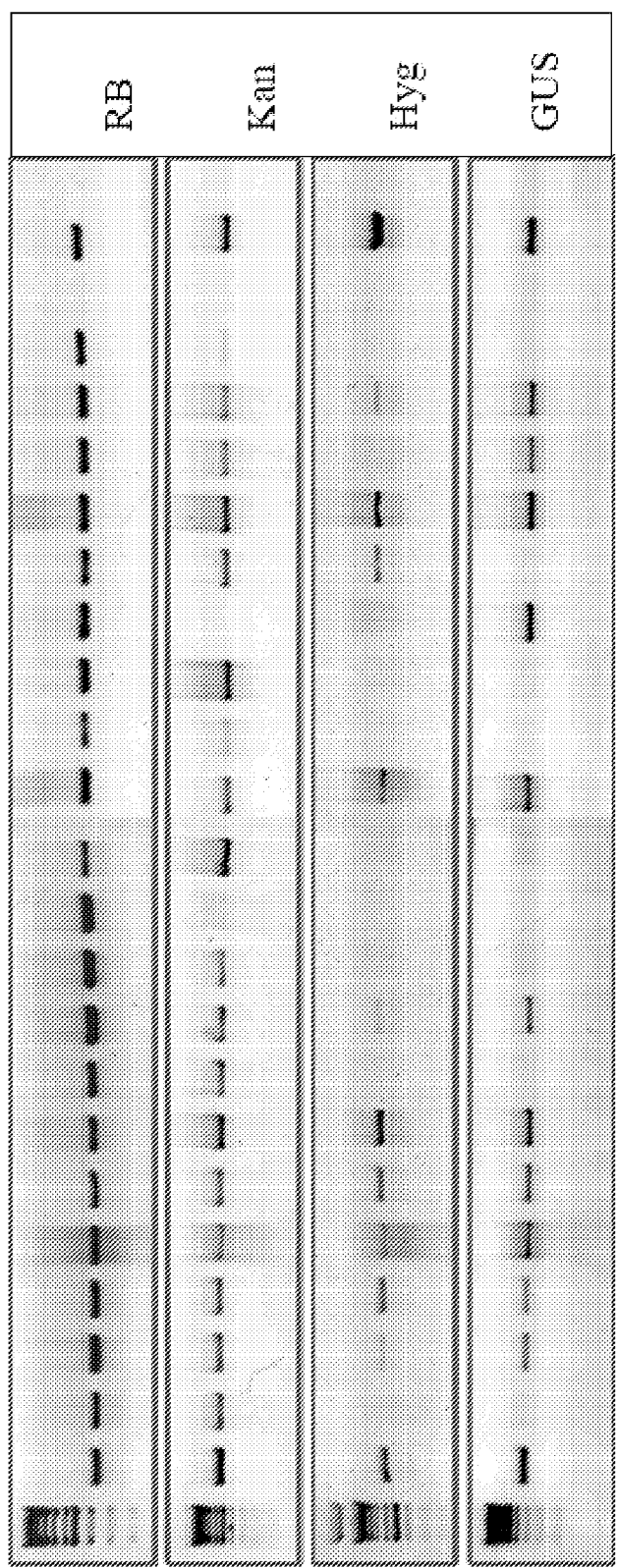
FIG. 6: PCR analysis of 21 transgenic *Solanum tuberosum* var. Maris Peer lines generated through *Ensifer*-mediated transformation (pC5105+pCDL04541) for the presence of the RB, nptII, hptII or GUSPlus transgene. Lanes 1-21 refer to DNA extracts from individual potato leaves. Lane 22 is the plant negative control (un-treated Maris Peer), lane 23 is the plasmid positive control (pC5105/pCDL04541) while lane 24 shows the no template control.

The presence of four transgenes (RB, Kan, Hyg and GUS) was examined in the transgenic potato lines and it was found that there are different combinations of transgenes within different lines (FIG. 6). The most interesting is that multiple lines carry all 4 possible transgenes (RB, Kan, Hyg and GUS), indicating that *Ensifer* mediated transformation can be used for co-transformation purposes, which is critical for the inclusion of multiple traits (i.e. 'gene stacking') into the targeted plant genome.

Figure 7:
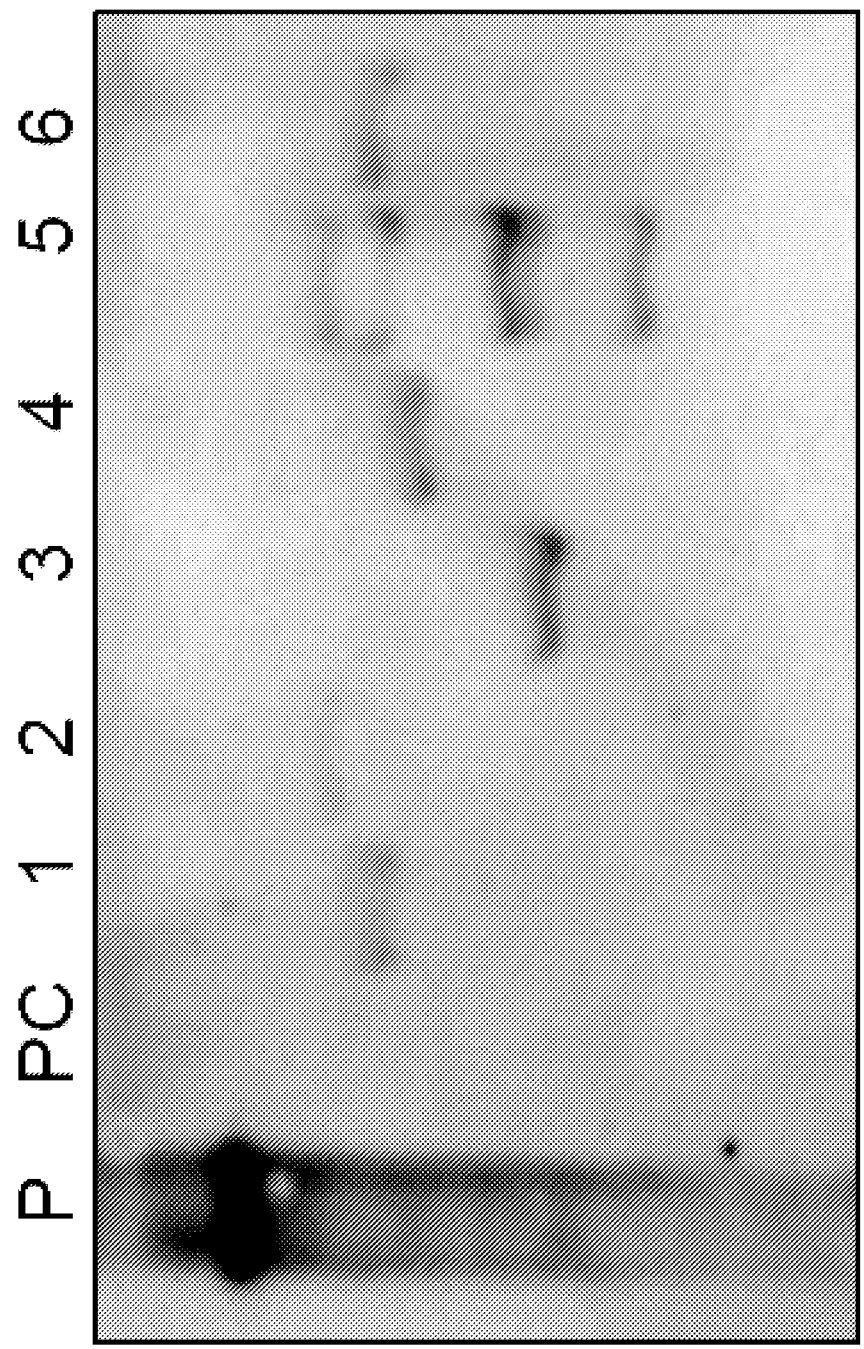
FIG. 7: Analysis of stable, genomic integration and copy number of the late blight resistance gene (RB) via southern hybridization. Lanes 1-6 show EcoR1-digested *Solanum tuberosum* var. Maris Peer DNA of six individual transgenic lines (RB2-RB9) generated through *Ensifer*-transformation. Untreated Maris Peer served as potato negative control (PNC) while digested pCDL04541 was used as plasmid positive control.

Southern hybridization on a select number of lines confirmed the stable integration of the RB transgene into the potato lines (FIG. 7).

Figure 8:
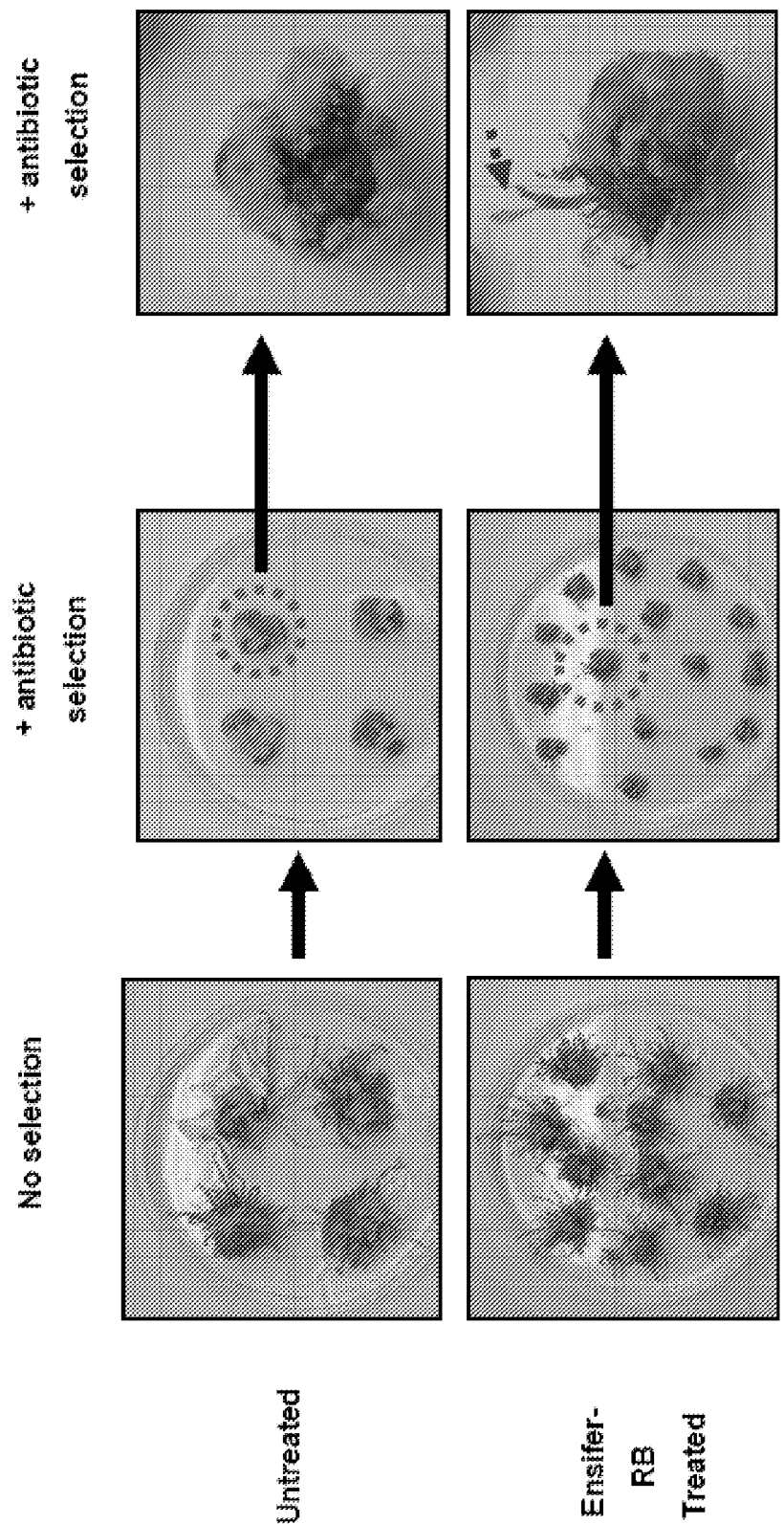
FIG. 8: Potential for *Ensifer* to transform potato tissue in the absence of an exogenous Ti plasmid. Explants were un/treated with *Ensifer*-RB and differentiating calli incubated in the presence of antibiotic selection (25 ug/ml kanamycin). Selection prohibited shoot emergence in untreated control. Shoots evident (red arrow) in *Ensifer*-RB treated explants in presence of selection agent.

Surprisingly, it was discovered that in the absence of the Ti plasmid (pC5105, containing the pre-requisite virulence genes to facilitate gene transfer), *Ensifer adhaerens* (i.e. *Ensifer* RB) has the potential to deliver transgenes in to a target genome (FIG. 8). Although inefficient compared to ATMT, this demonstrates that *Ensifer* in its wild type form possesses the basic genetic machinery required for transformation.

Efficacy of alternative *Ensifer adhaerens* strains to transform plant genomes in comparison to strain *E. adhaerens* OV14 (NCIMB Accession Number 41777, deposited with a recognised International Depostiary Authority on 18 Nov. 2010 in compliance with the Budapest Treaty)

A total of seven strains of *Ensifer adhaerens* were obtained from the NCIMB (Accession Number: 12342) and the Belgian co-ordinated collections of micro-organisms at the University of Ghent (LMG 9954, LMG 10007, LMG 20216, LMG 20571, LMG 20582, LMG 21331). All seven trains were cultured as directed from the supplier, however only *E. adhaerens* LMG 10007, LMG 9954, LMG 20582 and LMG 20216 grew successfully. These 4 strains were verified as *E. adhaerens* using primers (LEFT: tcggaattactgggcgtaaa (SEQUENCE ID NO: 6) and RIGHT: cgaactgaaggaatacatctctg-taat (SEQUENCE ID NO: 7)) specific for *E. adhaerens* when compared to *Agrobacterium tumefaciens* strain c58, based on 16S rRNA region. Partial sequencing (from 588 bp to 688 bp) of 16S rRNA highlighted the similarity (>98.63%) of the 4 additional *E. adhaerens* strains with *E. adhaerens* OV14 (Table 1). The 16S rRNA gene sequences for LMG 9954, LMG 20582, LMG 20216 and LMG 1007 are provided in SEQUENCE ID NOs: 2 to 5, respectively.

Figure 9:
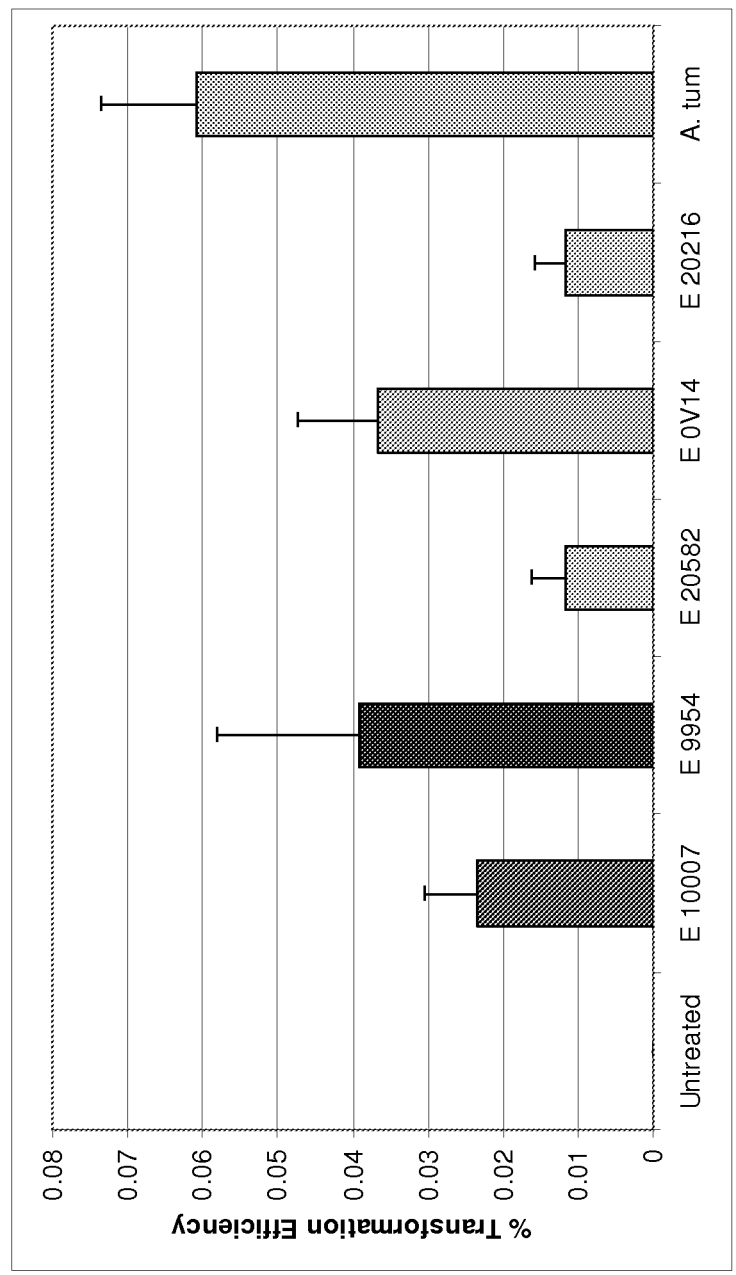
FIG. 9: Comparative transformation efficiency of 4 alternative *E. adhaerens* strains compared to the strain *E. adhaerens* OV14 (NCIMB Accession Number 41777, deposited with a recognised International Depositary Authority on 18 Nov. 2010 in compliance with the Budapest Treaty) and *A. tumefaciens*. T0 seeds were obtained from mature *Arabidopsis* plants in planta transformed with the respective bacterial solution. Seed collected from two independent experiments were surface sterilized and plated on MS media supplemented with 50 µg/ml hygromycin.

These four strains in addition to *E. adhaerens* OV14 (E OV14) and *A. tumefaciens* AGL1 were tested for their propensity to genetically transform the model plant species *Arabidopsis thaliana* using the standard floral dip protocol (Clough and Bent, 1998); with each strain equipped with the transformation vector pCAMBIA 5105. Data collected from a replicated experiment confirmed the transformation ability (confirmed by growth of $T_0$ seedlings on MS media supplemented with 50 μg/ml hygromycin) of *Ensifer adhaerens* OV14 relative to that of *Agrobacterium*. Significantly, E9954 was of comparative equivalence to EOV14 in its ability to transform *Arabidopsis* (FIG. 9). E9954 is 99.2% similar to EOV14 at the DNA level. Of the remaining 3 *E. adharens* strains, transgenic *Arabidopsis* seedlings were recovered from each treatment but their efficacy was substantially less than EOV14 and E9954, relative to *Agrobacterium tumefaciens*.

TABLE 1

Partial sequencing (from 588bp to 688bp) of 16S rRNA
highlighted the similarity (>98.63%) of the 4 additional
E. adhaerens strains with E. adhaerens OV14
CLUSTAL 2.0.12 multiple sequence alignment

```
16SrDNA_OV14_
GCCTGATCAGCCATGCCGCGTGAGTGATGAAGGCCCTAGGGTTGTAAAGCTCTTTCACCG 60
E OV14            ---------GCC-
TGCCGCGTGAGTGATGANGGCCCTAGGGTTGTAAAGCTCTTTCACCG 50
E9954F-16SF       -GCTGNTCNGCC-
TGCCGCGTGAGTGATGANGGCCCTAGGGTTGTAAAGCTCTTTCACCG 58
E20582F-16SF      ----------------------------------------------------------
--
E20216F-16SF      ----------------------------------------------------------
--
E10007F-16SF      ----------------------------------------------------------
CG 2
AGF-16SF          -----------
CACGCCGCGTGAGTGATGANGGTCTTCGGATCGTAAAACTCTGTTATTA 49

16SrDNA_OV14_     GTGAAGA---------TAA----------------
TGACGGTAACCGGAGAAGAAGCCCC 95
E OV14            GTGAAGA---------TAA----------------
TGACGGTAACCGGAGAAGAAGCCCC 85
E9954F-16SF       GTGAAGA---------TAA----------------
TGACGGTAACCGGAGAAGAAGCCCC 93
E20582F-16SF      -TGAAGA---------TAA----------------
TGACGGTAACCGGAGAAGAAGCCCC 34
E20216F-16SF      ---------------------------------------------
GAGAAGAAGCCCC 13
E10007F-16SF      GTGAAGA---------TAA----------------
TGACGGTAACCGGAGAAGAAGCCCC 37
AGF-16SF
GGGAAGAACATACGTGTAAGTAACTATGCACGTCTTGACGGTACCTAATCAGAAAGCCAC 109
                                                    *  *****
*

16SrDNA_OV14_     GGCTAACTT-
CGTGCCAGCAGCCGCGGTAATACGAAGGGGGCTAGCGTTGTTCGGAATTA 154
E OV14            GGCTAACTT-
CGTGCCAGCAGCCGCGGTAATACGAAGGGGGCTAGCGTTGTTCGGAATTA 144
E9954F-16SF       GGCTAACTT-
CGTGCCAGCAGCCGCGGTAATACGAAGGGGGCTAGCGTTGTTCGGAATTA 152
E20582F-16SF      GGCTAACTT-
CGTGCCAGCAGCCGCGGTAATACGAAGGGGGCTAGCGTTGTTCGGAATTA 93
E20216F-16SF
GGCTAACTTTCGTGCCAGCAGCCGCGGTAATACGAAGGGGGCTAGCGTTGTTCGGAATTA 73
E10007F-16SF      GGCTAACTT-
CGTGCCAGCAGCCGCGGTAATACGAAGGGGGCTAGCGTTGTTCGGAATTA 96
AGF-16SF          GGCTAACTA-
CGTGCCAGCAGCCGCGGTAATACGTAGGTGGCAAGCGTTATCCGGAATTA 168
                  ********  **********************  ***  ***  ******  *
********

16SrDNA_OV14_
CTGGGCGTAAAGCGCACGTAGGCGGACATTTAAGTCAGGGGTGAAATCCCAGAGCTCAAC 214
E OV14
CTGGGCGTAAAGCGCACGTAGGCGGACATTTAAGTCAGGGGTGAAATCCCAGAGCTCAAC 204
E9954F-16SF
CTGGGCGTAAAGCGCACGTAGGCGGACATTTAAGTCAGGGGTGAAATCCCGGGGCTCAAC 212
E20582F-16SF
CTGGGCGTAAAGCGCACGTAGGCGGACATTTAAGTCAGGGGTGAAATCCCGGGGCTCAAC 153
E20216F-16SF
CTGGGCGTAAAGCGCACGTAGGCGGACATTTAAGTCAGGGGTGAAATCCCGGGGCTCAAC 133
E10007F-16SF
CTGGGCGTAAAGCGCACGTAGGCGGACATTTAAGTCAGGGGTGAAATCCCGGGGCTCAAC 156
AGF-16SF
TTGGGCGTAAAGCGCGCGTAGGCGGTTTTTTAAGTCTGATGTGAAAGCCCACGGCTCAAC 228
                 **************  *********        *******  *   ******  ***
*******

16SrDNA_OV14_
TCTGGAACTGCCTTTGATACTGGGTGTCTAGAGTATGGAAGAGGTGAGTGGAATTCCGAG 274
E OV14
TCTGGAACTGCCTTTGATACTGGGTGTCTAGAGTATGGAAGAGGTGAGTGGAATTCCGAG 264
E9954F-16SF
CCCGGAACTGCCTTTGATACTGGGTGTCTAGAGTATGGAAGAGGTGAGTGGAATTCCGAG 272
E20582F-16SF
CCCGGAACTGCCTTTGATACTGGGTGTCTAGAGTATGGAAGAGGTGAGTGGAATTCCGAG 213
E20216F-16SF
```

TABLE 1-continued

Partial sequencing (from 588bp to 688bp) of 16S rRNA
highlighted the similarity (>98.63%) of the 4 additional
E. adhaerens strains with E. adhaerens OV14
CLUSTAL 2.0.12 multiple sequence alignment

```
CCCGGAACTGCCTTTGATACTGGGTGTCTAGAGTATGGAAGAGGTGAGTGGAATTCCGAG 193
E10007F-16SF
CCCGGAACTGCCTTTGATACTGGGTGTCTAGAGTATGGAAGAGGTGAGTGGAATTCCGAG 216
AGF-16SF
CGTGGAGGGTCATTGGAAACTGGAAAACTTGAGTGCAGAAGAGGAAAGTGGAATTCCATG 288
                     ***    * ** ** *****    ** ****   *******  **********
*

16SrDNA_OV14_
TGTAGAGGTGAAATTCGTAGATATTCGGAGGAACACCAGTGGCGAAGGCGGCTCACTGGT 334
E_OV14
TGTAGAGGTGAAATTCGTAGATATTCGGAGGAACACCAGTGGCGAAGGCGGCTCACTGGT 324
E9954F-16SF
TGTAGAGGTGAAATTCGTAGATATTCGGAGGAACACCAGTGGCGAAGGCGGCTCACTGGT 332
E20582F-16SF
TGTAGAGGTGAAATTCGTAGATATTCGGAGGAACACCAGTGGCGAAGGCGGCTCACTGGT 273
E20216F-16SF
TGTAGAGGTGAAATTCGTAGATATTCGGAGGAACACCAGTGGCGAAGGCGGCTCACTGGT 253
E10007F-16SF
TGTAGAGGTGAAATTCGTAGATATTCGGAGGAACACCAGTGGCGAAGGCGGCTCACTGGT 276
AGF-16SF
TGTAGCGGTGAAATGCGCAGAGATATGGAGGAACACCAGTGGCGAAGGCGACTTTCTGGT 348
     ***** ******** ** *** **  *********************** **
*****

16SrDNA_OV14_
CCATTACTGACGCTGAGGTGCGAAAGCGTGGGGAGCAAACAGGATTAGATACCCTGGTAG 394
E_OV14
CCATTACTGACGCTGAGGTGCGAAAGCGTGGGGAGCAAACAGGATTAGATACCCTGGTAG 384
E9954F-16SF
CCATTACTGACGCTGAGGTGCGAAAGCGTGGGGAGCAAACAGGATTAGATACCCTGGTAG 392
E20582F-16SF
CCATTACTGACGCTGAGGTGCGAAAGCGTGGGGAGCAAACAGGATTAGATACCCTGGTAG 333
E20216F-16SF
CCATTACTGACGCTGAGGTGCGAAAGCGTGGGGAGCAAACAGGATTAGATACCCTGGTAG 313
E10007F-16SF
CCATTACTGACGCTGAGGTGCGAAAGCGTGGGGAGCAAACAGGATTAGATACCCTGGTAG 336
AGF-16SF
CTGTAACTGACGCTGATGTGCGAAAGCGTGGGGATCAAACAGGATTAGATACCCTGGTAG 408
     *   * ***********  ***************
************************

16SrDNA_OV14_       TCCACGCCGTAAACGATGAATGTTAGCCGTCGGGCAGTTT--
ACTGTTCGGTGGCGCAGC 452
E_OV14              TCCACGCCGTAAACGATGAATGTTAGCCGTCGGGCAGTTT--
ACTGTTCGGTGGCGCAGC 442
E9954F-16SF         TCCACGCCGTAAACGATGAATGTTAGCCGTCGGGCAGTTT--
ACTGTTCGGTGGCGCAGC 450
E20582F-16SF        TCCACGCCGTAAACGATGAATGTTAGCCGTCGGGCAGTTT--
ACTGTTCGGTGGCGCAGC 391
E20216F-16SF        TCCACGCCGTAAACGATGAATGTTAGCCGTCGGGCAGTTT--
ACTGTTCGGTGGCGCAGC 371
E10007F-16SF        TCCACGCCGTAAACGATGAATGTTAGCCGTCGGGCAGTTT--
ACTGTTCGGTGGCGCAGC 394
AGF-16SF
TCCACGCCGTAAACGATGAGTGCTAAGTGTTAGGGGGTTTCCGCCCCTTAGTGCTGCAGC 468
                   ******************* ** **   ** ** ****   *   *  **
*****

16SrDNA_OV14_
TAACGCATTAAACATTCCGCCTGGGGAGTACGGTCGCAAGATTAAAACTCAAAGGAATTG 512
E_OV14
TAACGCATTAAACATTCCGCCTGGGGAGTACGGTCGCAAGATTAAAACTCAAAGGAATTG 502
E9954F-16SF
TAACGCATTAAACATTCCGCCTGGGGAGTACGGTCGCAAGATTAAAACTCAAAGGAATTG 510
E20582F-16SF
TAACGCATTAAACATTCCGCCTGGGGAGTACGGTCGCAAGATTAAAACTCAAAGGAATTG 451
E20216F-16SF
TAACGCATTAAACATTCCGCCTGGGGAGTACGGTCGCAAGATTAAAACTCAAAGGAATTG 431
E10007F-16SF
TAACGCATTAAACATTCCGCCTGGGGAGTACGGTCGCAAGATTAAAACTCAAAGGAATTG 454
AGF-16SF
TAACGCATTAAGCACTCCGCCTGGGGAGTACGACCGCAAGGTTGAAACTCAAAGGAATTG 528
           ********** ** *****************  ****** **
***************
```

TABLE 1-continued

Partial sequencing (from 588bp to 688bp) of 16S rRNA
highlighted the similarity (>98.63%) of the 4 additional
E. adhaerens strains with E. adhaerens OV14
CLUSTAL 2.0.12 multiple sequence alignment

```
16SrDNA_OV14_
ACGGGGGCCCGCACAAGCGGTGGAGCATGTGGTTTAATTCGAAGCAACGCGCAGAACCTT 572
E OV14
ACGGGGGCCCGCACAAGCGGTGGAGCATGTGGTTTAATTCGAAGCAACGCGCAGAACCTT 562
E9954F-16SF
ACGGGGGCCCGCACAAGCGGTGGAGCATGTGGTTTAATTCGAAGCAACGCGCAGAACCTT 570
E20582F-16SF
ACGGGGGCCCGCACAAGCGGTGGAGCATGTGGTTTAATTCGAAGCAACGCGCAGNACCTT 511
E20216F-16SF
ACGGGGGCCCGCACAAGCGGTGGAGCATGTGGTTTAATTCGAAGCAACGCGCAAAACCTT 491
E10007F-16SF
ACGGGGGCCCGCACAAGCGGTGGAGCATGTGGTTTAATTCGAAGCAACGCGCNNNACCTT 514
AGF-16SF
ACGGGGACCCGCACAAGCGGTGGAGCATGTGGTTTAATTCGAAGCAACGCGAAGAACCTT 588
                 ******  ************************************* 
*****

16SrDNA_OV14_
ACCAGCCCTTGACATCCCGATCGCGGATTACAGAGATGTATTCCTTCAGTTCGGCTGGAT 632
E OV14
ACCAGCCCTTGACATCCCGATCGCGGATTACAGAGATGTATTCCTTCAGTTCGGCTGGAT 622
E9954F-16SF
ACCAGCCCTTGACATCCCGATCGCGGATTACAGAGACGTTTTCCTTCAGTTCGGCTGGAT 630
E20582F-16SF
ACCAGCCCTTGACATCCCGATCGCGGATTACGGAGACGTTTTCCTTCAGTTCGGCTGGAT 571
E20216F-16SF
ACCAGCCCTTGACATCCCGATCGCGGATTACGGAGACGTTTTCCTTCAGTTCGGCTGGAT 551
E10007F-16SF
ACCAGCCCTTGACATCCCGATCGCGGATTANNNAGNTGTTTTCCTTCAGTTCGGCTGGAT 574
AGF-16SF            ACCAAATCTTGACATCCT--TTGACAACTCTAGAGATAGAGCCTTCCCCTTCGG--
GGGA 644
                    ****  **********   *    *  *   **       *  *   *****  **

16SrDNA_OV14_       CGGAG--ACAGGTGCTGCATGGCTGTCGTCAGCTCGTGTCGTGAGATGTTGGGT----
-- 684
E OV14              CGGAG--
ACAGGTGCTGCATGGCTGTCGTCAGCTCGTGTCGTGAGATGTTGGGTTAAGTC 680
E9954F-16SF         CGGAG--
ACAGGTGCTGCATGGCTGTCGTCAGCTCGTGTCGTGAGATGTTGGGTTAAGTC 688
E20582F-16SF        CGGAG--
ACAGGTGCTGCATGGCTGTCGTCAGCTCGTGTCGTGAGATGTTGGGTTAAGTC 629
E20216F-16SF        CGGAG--ACAGGTGCTGCATGGCTGTCGTCAGCTCGTGT-------------------
-- 588
E10007F-16SF        CGGNN--
ACAGGTGCTGCATGGCTGTCGTCAGCTCGTGTCGTGAGATGTTGGGTTAAG-- 630
AGF-16SF            CAAAGTGACAGGNGGTGCATGGTTGTCGTCAGCTCGTGTCGTGAGATGTTGGGTTNA-
-- 701
                      *   *****  * ******* ****************

16SrDNA_OV14_       -----------
E OV14              CCGCAACGAGA 691
E9954F-16SF         CCGCAA----- 694
E20582F-16SF        -----------
E20216F-16SF        -----------
E10007F-16SF        -----------
AGF-16SF            -----------
```

Propensity for E. adhaerens OV14 to Genetically Transform Wheat

Figure 10:
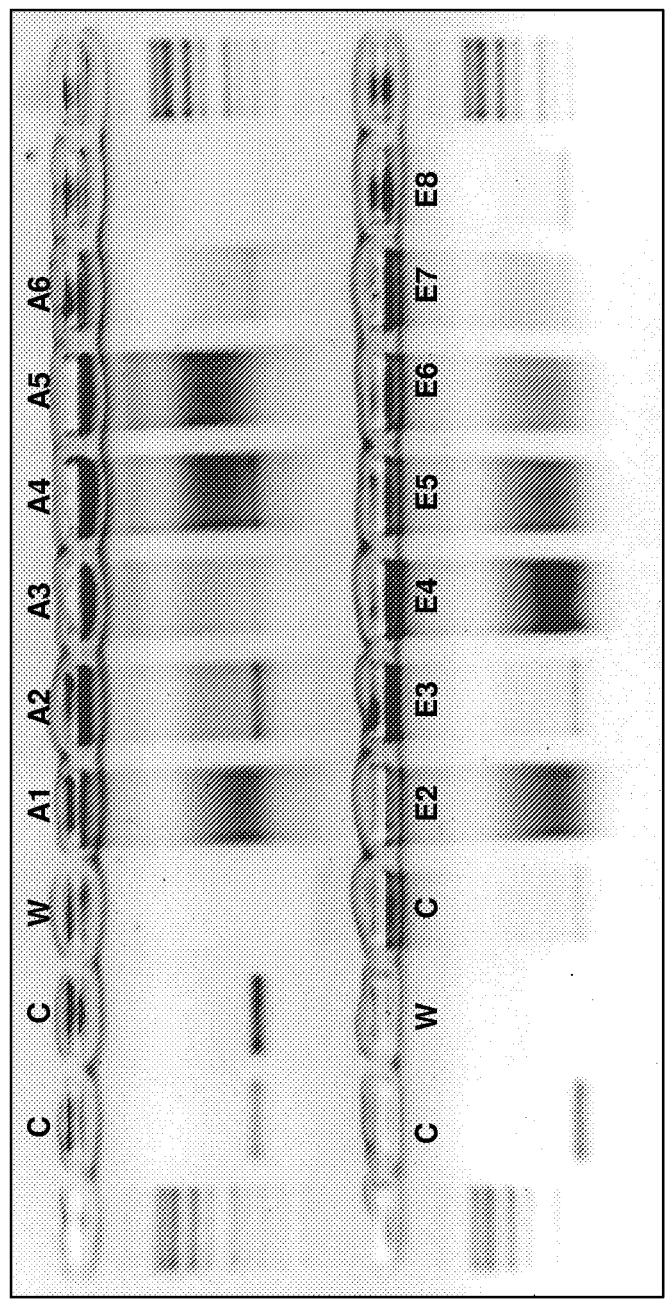
FIG. 10: PCR-based analysis of wheat plants derived from *A. tumefaciens* mediated transformation (A1-A6) and *E. adhaerens* OV14 treated lines (E2-E8). Presence of 345 bp band as evident in control (C) and not present in water (W) samples indicates the successful amplification of β-glucuronidase (GUS) reporter gene, which is resident on the pC5105 transformation vector.

To test the ability of E. adhaerens OV14 (containing pC5105) to successfully transform wheat, mature embryos excised from wheat were transformed as per procedure of Ding et al. (2009), with a separate group of mature embryos treated with A. tumefaciens AGL1 (containing pC5105) as a control. In the presence of the selection agent hygromycin, transgenic tissues were recorded from E. adhaerens OV14 treated explants. These were left to grow to maturity and transferred to the glasshouse. Tissue samples were collected, total DNA extracted and a qualitative detection of the β-glucuronidase (GUS) reporter gene completed via PCR (FIG. 10). As the GUS reporter gene resides within the T-DNA of pC5105, its presence/absence in the genomes of tested wheat seedlings substantiates whether they are transformed or not. As evident from FIG. 10, a band corresponding to the size of the vector control (C) was detected in E. adhaerens OV14 derived lines E3, E7 and E8. This was also the case in A. tumefaciens AGL1 derived lines A2, 3, 4 and 6. This confirms that E. adhaerens OV14 has the capacity to genetically transform wheat.

Confirmation that E. adhaerens OV14 can Genetically Transform Potato, Tobacco and Arabidopsis.

Figure 11:
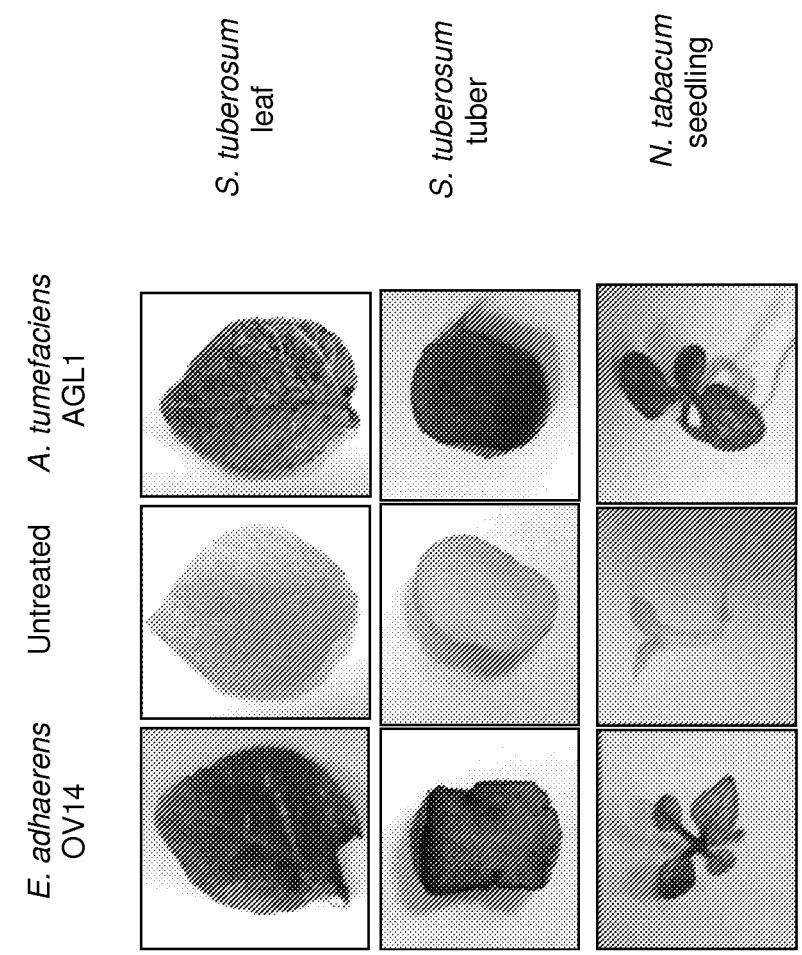
FIG. 11: Demonstrated transformation of tobacco and potato leaves and potato tuber tissues using *E. adhaerens* OV14 (NCIMB Accession Number 41777, deposited with a recognised International Depositary Authority on 18 Nov. 2010 in compliance with the Budapest Treaty) versus *A. tumefaciens* AGL1.

Based on previous protocols, tobacco and potato were genetically transformed with E. adhaerens OV14 and tested for the presence of β-glucuronidase (GUS) reporter gene activity. The ability of E. adhaerens OV14 to genetically transform potato is significant owing to previous reports on the recalcitrance of potato to non-*Agrobacterium* species (Wendt et al.). The GUS reporter gene resides within the T-DNA of pC5105 and gene activity is verified by the presence of a blue stain in treated tissues. As visualized in FIG. 11, GUS activity was recorded in leaf tissue of potato and tobacco. In addition, tubers harvested from the transformed potato lines also indicated the presence of GUS activity. This confirms the non-tissue specific capacity of *E. adhaerens* OV14 to genetically transform plant tissues and underlines its potential role in the delivery of plant derived pharmaceuticals, which require production in large storage tissues (e.g. potato tubers and tobacco leaves). The transformation efficiency at the callus- and shoot regeneration stage for the transformation of *Solanum tuberosum* via *Ensifer adhaerens*- and *Agrobacterium tumefaciens*-mediated transformation were significantly similar.

TABLE 2

Overview of transformation efficiencies at the callus- and shoot regeneration stage for the transformation of *Nicotiana tabacum* and *Solanum tuberosum* via Ensifer adhaerens- and *Agrobacterium tumefaciens*-mediated transformation.

| Treatment[a] | Crop | Total explants treated (independent experiments) | Transformation efficiency (%)[b] | |
|---|---|---|---|---|
| | | | Callus formation[1] | Shoot formation[2] |
| E. adhaerens | N. tabacum | 96 (3) | 35.16 (+/−9.3) | 20.91 (+/−4.7) |
| A. tumefaciens | | 75 (3) | 78.43 (+/−11.3) | 44.43 (+/−4.4) |
| E. adhaerens | S. tuberosum* | 40 (2) | 100 (+/−0) | 37.5 (+/−12.5) |
| A. tumefaciens | | 32 (2) | 100 (+/−0) | 51.67 (+/−6.6) |
| E. adhaerens | S. tuberosum** | 50 (2) | 80.0 (+/−20.0) | 33.33 (+/−6.6) |
| A. tumefaciens | | 32 (2) | 85.0 (+/−15.0) | 58.33 (+/−8.3) |

[a]Transformations were carried out using *E. adhaerens* strain OV14 and *A. tumefaciens* strain AGL1 harboring transformation vectors pCAMBIA5105 or pCAMBIA1305.2 respectively.
[b]Transformation efficiency was calculated based on the percentage of [1]explants that generated callus in the presence of the antibiotic and [2]explants that generated shoots in the presence of the antibiotic.
*Antibiotic selection regime: continuous selection with 10 μg/ml hygromycin B
**Antibiotic selection regime: continuous selection with 25 μg/ml hygromycin Experimental Genetic Transformation of Plant Tissue Via *Ensifer*-Mediated Transformation

*Arabidopsis* Transformation

For *Arabidopsis* in planta transformation *E. adhaerens* pC5105 was grown from a single colony in 400 ml Lurient Broth (LB, Sigma Aldrich) containing the appropriate antibiotics (50 μg/ml kanamycin, 200 μg/ml streptomycin, 200 μg/ml spectinomycin) at 28° C. and 200 RPM. Bacteria cells were centrifuge and the pellet resuspended in infiltration media [10× MS Media with Gamborg's vitamins; 1% Sucrose; 0.02% Silwet L-77; 0.1% MES; pH7.0]. Bacteria suspension was transferred to a small autoclave bag and plant material dipped into bacteria for 5-10 sec. Plants were covered with a plastic bag to maintain high humidity for 24 hours and were regularly watered afterwards. After 5 days plants were dipped again before they were left to set seeds. Mature seeds were harvested; surface sterilized and kept in 0.1% agar (Agar Technical No. 3) the fridge for 4 days afterwards to break dormancy. Seeds (5000) were spread onto Petri dishes (150 mm ø) on germination media [MS Media with Gamborg's vitamins (4.4 g/l); Sucrose (2.5%); Agar Technical No. 3 (8 g/l); 50 μg/ml hygromycin B; pH5.8], sealed and kept at 22° C. for 16/8 hours (day/night) until germination.

*Solanum tuberosum* Transformation

For transformation of *Solanum tuberosum*, *E. adhaerens* pC5105+pCDL04541 was grown from single colony in selective LB (50 μg/ml kanamycin, 200 μg/ml streptomycin, 200 μg/ml spectinomycin, 10 μg/ml tetracycline) at 28° C. and 220 RPM over night (or until $OD_{600\ nm}$>0.4). Bacteria cultures were centrifuged (4000 RPM, 30 min, 4° C.), re-suspended in co-cultivation media [MS Media with Gamborg's vitamins (4.4 g/l); Sucrose (3%); pH5.8] and the $OD_{600\ nm}$ adjusted to 0.8-1.0. Potato explants (internodal tissue) was cut into 3-5 mm fragments and transferred to pulse inducing media [MS Media with Gamborg's vitamins (4.4 g/l); L-Cysteine (40 μg/ml); ascorbic acid (15 μg/ml); NAA (30 μM); BAP (24 μM); trans-Zeatin-riboside (0.8 μg/ml); pH5.8]. Bacteria suspension and explants were incubated for 30 minutes (shaking gently), blot dried on sterile filter paper and transferred to non-selective callus inducing media (CIM) [MS Media with Gamborg's vitamins (4.4 g/l); trans-zeatin-riboside (0.8 μg/ml); Sucrose (3%); Agar technical No. 3 (0.6%); NAA (0.3 μg/ml); BAP (2.25 μg/ml); 2,4-D (0.05 μg/ml); pH5.8]. Plates were sealed, wrapped in tin foil and incubated at 22° C. for 72 hours. After that explants were washed [MS Media with Gamborg's vitamins (4.4 g/l); Sucrose (1%); MES (0.5 μg/ml); D-Mannitol (2%); cefotaxime (500 μg/ml); pH5.8] for 45 minutes (gentle shaking) and blot dried on sterile filter paper. Explants were placed on fresh, CIM plates [containing 50 μg/ml kanamycin] and weekly sub-cultured onto fresh selective CIM [excluding 2,4-D]. Explants with callus was transferred to selective shoot inducing media (SIM) [containing 50 μg/ml kanamycin] [MS Media with Gamborg's vitamins (4.4 g/l); trans-zeatin-riboside (0.8 μg/ml); Sucrose (3%); Agar technical No. 3 (0.6%); $GA_3$ (0.8 μg/ml); pH5.8] and sub-cultured regularly (every 14 days) or when shoots appeared. Shoots were excised and transferred to root inducing media (RIM) [containing 100 μg/ml kanamycin] [MS Media with Gamborg's vitamins (4.4 g/l); trans-zeatin-riboside (0.8 μg/ml); Sucrose (2.5%); Agar technical No. 3 (0.6%); pH5.8] in tissue culture pots and after 6 weeks transferred to the glasshouse.

*Nicotiana tabaccum* Transformation

*Nicotiana tabaccum* (cv Wisconsin 38) seeds were surface sterilized for 30 sec in 70% ethanol and than 10 min in 10% bleach before seeds were washed 5 times in sterile water. Seeds were placed on MS agar [MS Media with Gamborg's vitamins (2.2 g/l); Sucrose (1%); Agar technical No. 3 (0.8%); pH5.8] in a sterile tissue culture pot and germinated during a 16 hours light and 8 hours dark cycle at 22° C.

*E. adhaerens* pC5105 was grown from single colony in selective LB (50 μg/ml kanamycin, 200 μg/ml streptomycin, 200 μg/ml spectinomycin) at 28° C. and 220 RPM over night (or until $OD_{600\ nm}$>0.4). Bacteria cultures were centrifuged (4000 RPM, 30 min, 4° C.), re-suspended in co-cultivation media [MS Media with Gamborg's vitamins (4.4 g/l); Sucrose (3%); pH5.8] and the $OD_{600\ nm}$ adjusted to 0.8-1.0.

5-6 week old leaf material was cut into 5 mm squares transferred to induction media [MS Media with Gamborg's vitamins (4.4 g/l); Sucrose (3%); NAA (0.1 mg); BAP (1 mg); pH5.8]. Bacteria suspension and leaf fragments were incubated for 5 minutes (swirling), blot dried on sterile filter paper and transferred (adaxial side down) to non-selective regeneration media [MS Media with Gamborg's vitamins (4.4 g/l); Sucrose (3%); Agar technical No. 3 (0.6%); NAA (0.1 mg); BAP (1 mg); pH5.8]. Plates were sealed, wrapped in tin foil and incubated at 22° C. After 72 hours leaf fragments were placed onto selective regeneration media (abaxial side down) [MS Media with Gamborg's vitamins (4.4 g/l); Sucrose (3%); Agar technical No. 3 (0.6%); NAA (0.1 mg); BAP (1 mg); pH5.8; timentin (200 μg/ml); hygromycin B (50 μg/ml)] and incubated at 22° C. during a light (16 hours) and dark (8 hours) cycle. After that fragments were sub-cultured every 14 days onto fresh selective medium until shoots appear.

Shoots were collected and placed onto root inducing medium [MS Media with Gamborg's vitamins (4.4 g/l); Sucrose (3%); Agar technical No. 3 (0.6%); pH5.8; timentin (200 μg/ml); hygromycin B (50 μg/ml)] in sterile tissue culture pots and incubated at 22° C. (light 16 hours/dark 8 hours). Well developed plantlets were transferred to soil for further analysis.

The invention is not limited to the embodiment hereinbefore described which may be varied in construction and detail without departing from the spirit of the invention.

The invention claimed is:

1. A gene delivery method comprising:
   inoculating at least one plant cell with an isolated *Ensifer adhaerens* strain OV14 deposited under NCIMB Accession Number 41777, or an isolated variant thereof selected from the group consisting of *Ensifer adhaerens* strain LMG9954, LMG10007, LMG20582 and LMG20216, wherein said inoculating causes genetic transformation in said at least one plant cell, wherein said strain and variants of said strain have the ability to genetically transform an *Arabidopsis* plant with a transformation efficiency relative to *Agrobacterium tumefaciens* AGL1 of at least 15%.

2. The gene delivery method of claim 1, wherein said strain and variants of said strain have the ability to genetically transform an *Arabidopsis* plant with a transformation efficiency relative to *Agrobacterium tumefaciens* AGL1 of at least 50%.

3. The gene delivery method of claim 1, wherein in said at least one plant cell is from a plant selected from the group consisting of *Solanum tuberosum; Nicotiana tabaccum; Glycine max; Brassica napus*; wheat; barley; maize and rice.

4. The gene delivery method of claim 1, wherein the strain of *Ensifer adhaerens* OV14, or the isolated variant thereof, comprises a transformation platform including a transgene; wherein the transformation platform is a unitary transformation vector; and wherein the unitary transformation vector is selected from pC5105 or a functional variant thereof.

5. A method of producing a transgenic plant cell comprising:
   inoculating a cell with an isolated strain of *Ensifer adhaerens* OV14 deposited under NCIMB Accession Number 41777, or an isolated variant thereof selected from the group consisting of *Ensifer adhaerens* strain LMG9954, LMG10007, LMG20582 and LMG20216, and wherein the isolated strain of *Ensifer adhaerens* OV14, or the isolated variant thereof, contains a transformation platform including a transgene;
   culturing the cell under conditions that enable the strain of *Ensifer adhaerens* to transform the cell;
   selectively screening the inoculated cells for transformed cells;
   and isolating at least one transformed cell.

6. The method of claim 5, wherein said at least one transformed cell comprises a transgenic plant cell selected from the group consisting of *Solanum tuberosum; Nicotiana tabaccum; Glycine max; Brassica napus*; wheat; barley; maize and rice.

7. The method of claim 5, wherein the strain of *Ensifer adhaerens* OV14, or the isolated variant or progeny thereof, comprises a transformation platform including a transgene, wherein the transformation platform is a unitary transformation vector, and wherein the unitary transformation vector is selected from pC5105 or a functional variant thereof.

8. The method of claim 5, further comprising the step of developing at least one stable transformed plant from said at least one transformed cell.

9. An isolated *Ensifer adhaerens* strain OV14 deposited at the NCIMB on 18 Nov. 2010 under reference NCIMB 41777, and isolated variants thereof selected from the group consisting of *Ensifer adhaerens* strain LMG9954, LMG10007, LMG20582 and LMG20216, said strain and said variants having the ability to genetically transform an *Arabidopsis* plant with a transformation efficiency relative to *Agrobacterium tumefaciens* strain AGL1 of at least 50%, wherein said strain and said variants contain a transformation vector comprising a Ti plasmid, and one or more virulence genes.

10. The isolated *Ensifer adhaerens* strain of claim 9, wherein said strain and variants of said strain have the ability to genetically transform an *Arabidopsis* plant with a transformation efficiency relative to *Agrobacterium Tumefaciens* strain AGL1 of at least 60%.

11. The isolated *Ensifer adhaerens* strain of claim 9, wherein said transformation vector further comprises a transgene.

12. The isolated *Ensifer adhaerens* strain of claim 9, wherein the transformation platform is a unitary transformation vector or a binary transformation system.

13. The isolated *Ensifer adhaerens* strain of claim 12, wherein the unitary transformation vector is selected from pC5105 or a functional variant thereof.

14. An isolated *Ensifer adhaerens* strain OV14 deposited at the NCIMB on 18 Nov. 2010 under reference NCIMB 41777, and isolated variants thereof selected from the group consisting of *Ensifer adhaerens* strain LMG9954, LMG10007, LMG20582 and LMG20216, the strain containing a transformation vector comprising a Ti plasmid, a transgene, and one or more virulence genes.

15. The isolated *Ensifer adhaerens* strain of claim 14, wherein the transformation vector is a unitary transformation vector or a binary transformation system.

16. The isolated *Ensifer adhaerens* strain of claim 15, wherein the unitary transformation vector is selected from pC5105 or a functional variant thereof.

* * * * *